United States Patent [19]

Austin

[11] Patent Number: 5,076,269

[45] Date of Patent: Dec. 31, 1991

[54] APPARATUS FOR RETENTION OF AN ENDOTRACHEAL TUBE

[76] Inventor: Gregory A. Austin, 846 Bush St., Apt. 22, San Francisco, Calif. 94108

[21] Appl. No.: 399,765

[22] Filed: Aug. 28, 1989

[51] Int. Cl.$^5$ .............................................. A61M 16/00
[52] U.S. Cl. ........................ 128/207.17; 128/207.14; 128/163; 128/DIG. 26
[58] Field of Search ................ 128/207.17, 207.14, 128/DIG. 26, 163, 164, 169, 155; 604/179, 180, 389

[56] References Cited

U.S. PATENT DOCUMENTS

| | | | |
|---|---|---|---|
| 3,924,636 | 12/1975 | Addison | 128/351 |
| 3,927,676 | 12/1975 | Schultz | 128/351 |
| 4,249,529 | 2/1981 | Nestor et al. | 128/207.17 |
| 4,331,143 | 5/1982 | Foster | 128/207.17 |
| 4,351,331 | 9/1982 | Gereg | 128/207.17 |
| 4,392,857 | 7/1983 | Beran | 604/179 |
| 4,449,527 | 5/1984 | Hinton | 128/207.17 |
| 4,483,337 | 11/1984 | Clair | 128/207.17 |
| 4,592,351 | 6/1986 | Smith et al. | 128/207.17 |
| 4,774,944 | 10/1988 | Mischinski | 128/207.17 |

*Primary Examiner*—Edgar S. Burr
*Assistant Examiner*—Stephen R. Funk
*Attorney, Agent, or Firm*—Thomas M. Freiburger

[57] ABSTRACT

An endotracheal tube retaining apparatus includes a soft, flexible plate for engaging against the patient's upper lip, with a ring fastener for connecting the soft plate to the endotracheal tube. The ring fastener preferably can be engaged using one hand. For retaining the lip-engaging plate in a position to hold the tube properly against the patient's palate, a band of tape is provided to connect to the plate and to extend around the patient's head. The tape preferably has adhesive covering substantially all of one surface, but with the adhesive covered by a series of discrete release strips so that it can be exposed to adhere to the skin only in selected portions as appropriate. Adhesive contact with the hair is avoided. The band of tape is disposable and can be easily changed whenever necessary for comfort to the patient and proper positioning of the tube.

7 Claims, 5 Drawing Sheets 5,076,269

APPARATUS FOR RETENTION OF AN ENDOTRACHEAL TUBE

BACKGROUND OF THE INVENTION

This invention relates to medical apparatus generally, and more specifically it relates to an improved device for retention of an endotracheal tube in proper position on a patient, with convenience to the technician, comfort to the patient, and versatility in the ability to relocate the endotracheal tube periodically as needed.

In respiratory therapy, endotracheal tube therapy is a necessary but usually highly uncomfortable part of a patient's treatment. It has been typical and conventional practice to tape these endotracheal tubes on the patient, in a position intended to hold the tube properly in the patient's throat. In oral intubation, this usually requires that the tube be secured up toward the top of the mouth, generally against the palate and to one side of the mouth in order to allow the tongue some freedom. The tube must be held in a stable manner for comfort to the patient and effectiveness of the tube therapy.

There has generally not been a uniform method for securing the tubes in place, and different therapists have followed different practices in taping the tube to the patient. Sometimes these retention arrangements are effective and sometimes not, but in nearly all cases, the taped-in tube is uncomfortable to the patient and limited in effectiveness.

Further, there is ordinarily a need to change the tape quite frequently, for several reasons including resecuring of the tube in the proper position, discomfort of the patient and avoidance of lesions on the skin.

It is rather critical that the endotracheal tube be held at the correct level in the throat and at the right position. If the tube is central and extends too far down the throat, it may enter the right main stem bronchus, resulting in irritation and one-sided ventilation. If the tube does not extend far enough down the patient's throat, then it may not make a proper seal and it may pull out of the throat, preventing its effectiveness. Generally, the lower end of the endotracheal tube should extend to a point about three to five centimeters above the carina or bronchial bifurcation for best results. A radiopaque dye line in the tube allows the use of X-ray for locating the tube.

A number of attempts have been made previously to remedy these problems and to provide retaining devices for endotracheal tubes which will hold the tube securely and reliably in the correct position. Previous U. S. Pats. on this subject include Andrew Pat. Nos. 3,602,227 and 3,760,811, Cussell Patent No. 3,993,081, Nestor Patent No. 4,249,529, Hall Patent No. 4,284,076, Gereg Patent No. 4,351,331, George Patent No. 4,392,858, Hinton Patent No. 4,449,527, Clair Patent No. 4,483,337, Laird Patent No. 4,683,882 and McGinnis Patent No. 4,744,358.

Nearly all of the devices proposed in these patents would be highly uncomfortable to the patient, and most involve bulky apparatus for engaging the tube and for connecting to the patient. Some of the proposed apparatus would block the patient's mouth excessively (on oral intubation), would result in lesions developing on the patient's skin, would apply pressure due to the use of elastic, would prevent nearly all freedom of movement of the patient, or in some cases, would not be effective in holding the tube in the proper position.

The Hinton patent discloses an endotracheal tube retention system including a tube-engaging clamp and a strap which connects to both sides of the clamp via snap fasteners. The strap is in two pieces with a Velcro connection at the back to provide adjustable head size. However, the device of the Hinton patent would not secure the endotracheal tube near the top of the mouth, as is most desirable. If the elastic headband were tightened, it would tend to draw the clamp device back against the mouth, not toward the top of the mouth. In addition, the interior of Hinton's clip was of spongy material, which should be avoided for hygiene reasons. Further, the clamp device of the patent would significantly obstruct the patient's mouth at the lower side of the tube.

The Laird patent shows a somewhat similar endotracheal tube retaining apparatus, with a short strip of adhesive for engaging the patient's face. The tube engaging clamp of that patent is so bulky as to provide excessive obstruction of the mouth.

In the Nestor patent, a pair of bands are disclosed for extending around the back of the head, but the important upper band would tend to slip down, changing the position of tube retention. Further, the tube securing clamp device of this patent was of excessive size, engaging a large portion of the patient's upper lip and face and tending to obstruct the patient's mouth.

The endotracheal tube holder disclosed in the Cussell patent involved a large, obstructing clamp and adhesive tape applied to the upper lip of the patient, which is undesirable for comfort of the patient and reliability of the tube position.

The Andrew patents disclose endotracheal tube clamp structures which are large and obstructive and would tend not to secure the tube toward the patient's palate or maxillary as is desirable. Discomfort would be caused by rigid materials against or near the patient.

The Clair patent disclosed another endotracheal tube retainer which would seem to require a special tube end, which would not secure the tube upwardly toward the palate or maxillary and which would provide a hard line of contact against the patient's mouth.

The McGinnis device was quite bulky in obstructing the mouth and in requiring a relatively large and complex head gear for holding the tube in place.

The Gereg patent disclosed a tube holder which included a bite block and provision for connection around the ears. This would tend to cause discomfort and lesions on the patient.

As is clear from a review of these previous patents, the prior art has failed to adequately address a number of problems: maximizing comfort to the patient; proper retention of the endotracheal tube upwardly near or against the palate or maxillary; minimization of size of tube retention structure at the patient's mouth and face so as to maximize the ability of the patient to use the mouth; effectiveness in engaging the head and in holding the tube properly; ease of changing the headband retention structure; and avoidance of any rigid parts against the patient's upper lip. These problems are all addressed in an efficient device according to the present invention described below.

SUMMARY OF THE INVENTION

An endotracheal tube retaining apparatus in accordance with the present invention is quickly and easily used and is economical in manufacture and use. The device is reliable in holding the endotracheal tube up near the palate or maxillary and provides for maximum comfort to the patient. Use of the patient's mouth is optimized in an oral intubation, with greater ability to administer oral medication during tube therapy.

In accordance with the invention, the endotracheal tube retaining apparatus has a soft, rubbery lip-engaging plate or member for engaging against the patient's upper lip when the device is used for oral intubation. The rubbery member engages against a relatively small area above the mouth and just below the nasal openings. Adhesive is avoided in this area.

This soft rubbery member has a collar at its bottom edge, subtending only a portion of a circle for engaging against an upper arc of the cylindrical endotracheal tube. A low-profile clamp member, preferably of the type that can be installed with one hand, is used to clamp the tube in place against the collar. The collar acts as a small saddle engaging the upper side of the tube. Thus, there is virtually no protruding structure at left or right or below the endotracheal tube, so that minimal obstruction of the patient's mouth occurs.

The soft rubbery lip-engaging member preferably has a pair of openings or slots in left and right wings of the member. These are used to attach the device in place on the patient.

A tape band is provided for extending around the back of the patient's head, of sufficient length to extend around the head and to be connected to the wings of the soft lip-engaging member. The tape band preferably is a thin plastic disposable item having one surface coated with adhesive through at least most of its length. On the adhesive-coated surface are a series of separately removable discrete release strips covering the adhesive. Thus, the release strips may be separately removed to selectively engage against the patient's head at appropriate locations as desired for comfort and reliable retention. Although the tape band extends around the back of the head, no adhesive contacts the patient's hair.

In a preferred embodiment, the tape band has ends of narrowed width for connection with the lip-engaging member and is coated with adhesive at these ends. This enables the adhesive-coated ends to be placed through the slots in the lip-engaging member and then adhered back against itself to secure the member in place. The tape band preferably has extra length, so that one or both ends can be cut off as necessary for the head size of the particular patient.

With the tape band as described, the lip-engaging member can be held precisely as desired for appropriate tube positioning adjacent to the maxillary and for maximum comfort to the user. In one preferred embodiment only selected areas of the adhesive need be exposed, so that adhesive is avoided at the patient's hair and sufficient engagement can be made against the skin of the cheeks and below the ears in optimum locations on the skin for reliably holding the tube at the proper location.

In addition, the inexpensive and simple tape band can be removed and easily replaced with a new tape band as often as desired for comfort of the patient and for assuring continued accurate positioning of the endotracheal tube. The retention apparatus on the tube is easily wiped clean and need not be removed when the tape band is changed.

The retention system of the invention provides versatility in other ways as well. For example, a gauze pad can easily be split and slipped around the tube to be placed between the patient's lip and the retention device for situations where the patient has a cold sore or other lip lesion. Further, with prior procedures it was generally not possible to use gloves, but the method and system of this invention can easily be implemented using gloves.

It is therefore among the objects of the present invention to provide an endotracheal tube retention device with a combination of features which provides for greatly increased reliability and patient comfort, with minimal upsetting obstruction to the patient. These and other objects, advantages and features of the invention will be apparent from the following description of a preferred embodiment, considered along with the accompanying drawings.

DESCRIPTION OF PREFERRED EMBODIMENTS

Figure 1:
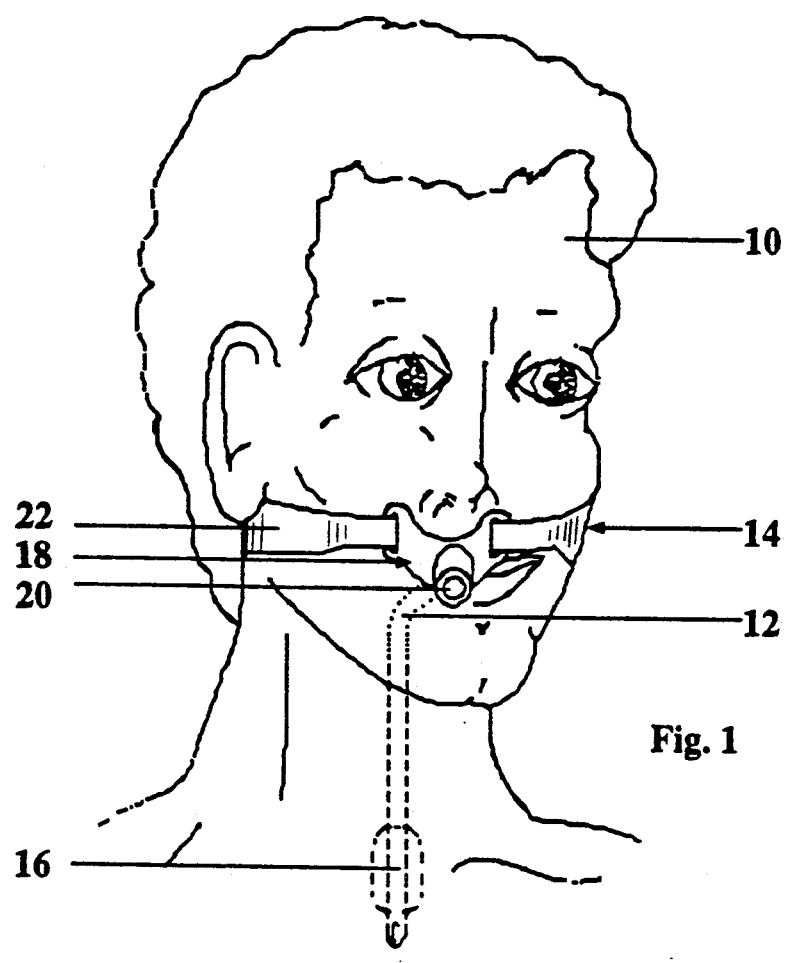
FIG. 1 is a perspective view showing a patient wearing an endotracheal tube retention apparatus in accordance with the principles of the invention.

In the drawings, FIG. 1 shows an endotracheally intubated patient 10 fitted with an endotracheal tube 12 retained in position on the patient using a tube retention apparatus and system 14 in accordance with the present invention.

As indicated in FIG. 1, the endotracheal tube is of conventional construction, with an inflatable bladder or cuff 16 for engaging the throat to seal the tube in place, and with an extending outer end positioned for connection to appropriate apparatus, not shown.

Although the apparatus of the invention is shown without a bite block, a bite block can easily be used over the tube behind the retention device 14, to prevent pinching or damaging of the tube 12 by the patient.

As shown in FIGS. 1 through 6, the tube retaining apparatus 14 includes a relatively small flexible lip-engaging member 18, a ring clamp 20 for firmly securing the member 18 to the endotracheal tube 12, and a tape band 22 for extending around the patient's head and adhering to the skin in appropriate locations for reliably holding the tube in the proper place.

Figure 2:
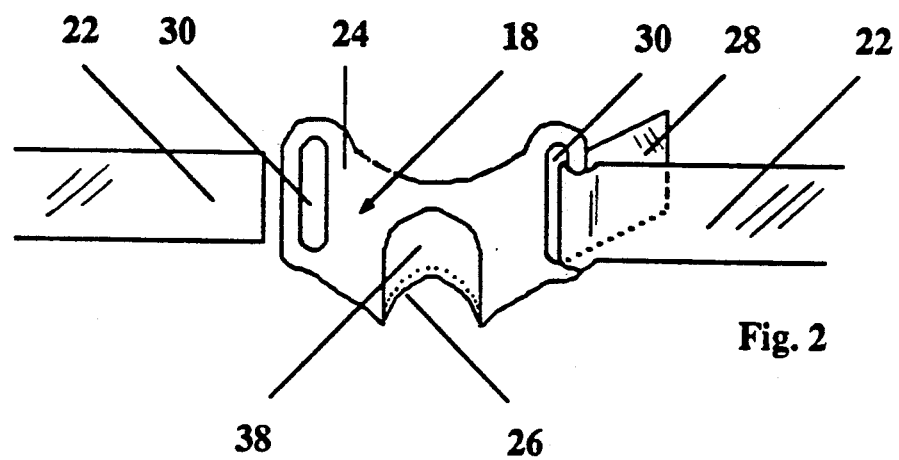
FIG. 2 is a view showing a soft flexible lip-engaging member which forms a part of the invention.

FIG. 2 shows the lip-engaging member 18 in greater detail. Preferably the member 18 includes a soft, rubbery lip-engaging plate 24 for engaging against the patient between the upper lip and the nasal openings. The soft plate 24 is quite small in dimensions for added comfort to the patient, and may be, for example, about 1½ inch in width and less than one inch in height.

To the soft plate 24 is preferably integrally secured a tube engaging collar 26 which in preferred embodiments is generally arcuate and extends through less than a full circle. It may extend through approximately 180° or less, for engaging in the manner of a saddle against the upper side of the tube just outside the patient's mouth. Although the collar 26 could define a full circle, it is preferable that the collar engages only the upper side of the tube as shown, for several reasons. By subtending only a limited arc, the collar can be nearly universal in fitting against a series of different endotracheal tube diameters. Also, the limited arc avoids any collar structure at the lower side of the tube, which would provide additional structure in front of and obstructing the patient's mouth.

The lip-engaging member 18 preferably is formed integrally, and may advantageously be molded from silicone or other suitable rubbery plastic material.

FIG. 2 also shows the connection of one end 28 of the tape band 22 through a slotted opening 30 in the lip-engaging member 18. As illustrated, the soft patient-engaging plate portion 24 of the member 18 preferably has left and right side wings with these generally vertically extending slots 30. The terminal ends of the tape band 28 are tapered to narrower widths so that they may pass through the slotted openings 30 to secure the member 18 in place on the patient. As illustrated in FIG. 2, the end 28 of the tape band, with adhesive exposed, may be put through the slot 30 and adhered against itself, for a secure retention.

Figure 3:
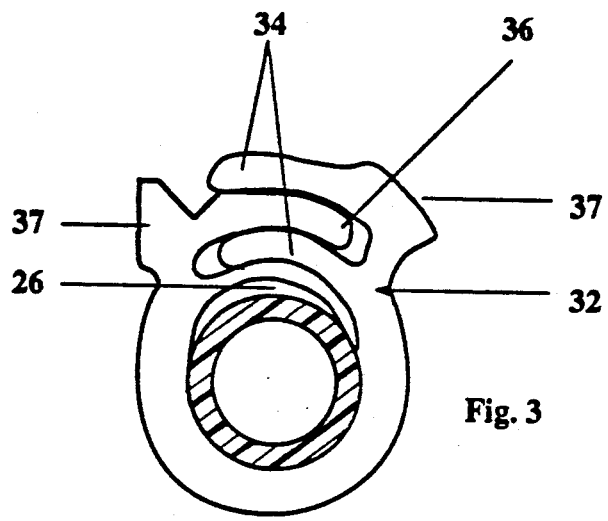
FIG. 3 is a view partially in section, showing a type of ring clamp which may be used with the lip-engaging member, for connection to an endotracheal tube.

FIG. 3 shows one example of a preferred form of ring clamp 32 which may be used with and form a part of the present invention. The ring clamp 32 is of a tough plastic material and is of relatively small dimension in comparison with its strength.

FIG. 3 shows that this ring clamp 32 may have a pair of gripping fingers 34 at one end between which is springingly received a tab 36 from the other end of the clamp. The clamp grips the collar or saddle 26 of the lip-engaging member 18 against the endotracheal tube 12, shown in cross-section in FIG. 3.

The clamp may engage against the tube through generally about 180° of the tube, and engages the outside of the collar 26 at the remainder of the annulus of its grip.

The type of ring clamp 32 illustrated is easily pushed and locked together with one hand, as by pinching gripping areas 37 between two fingers of the hand to engage the tab 36 between the fingers 34 of the clamp. Rachet-like teeth of the tab and one of the fingers engage together to prevent the ring clamp from slipping toward the open position.

Figure 3A:
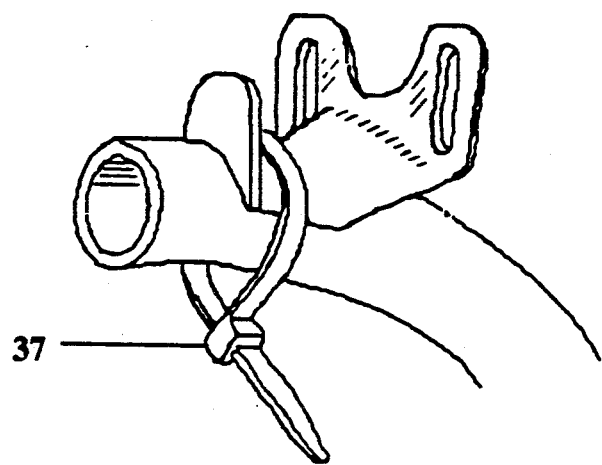
FIG. 3A is a view similar to FIG. 3, but showing a harness tie used in lieu of the ring clamp.

As an alternative to the ring clamp 32 shown in FIG. 3, a harness tie 37a can be applied around the collar and tube as shown in FIG. 3A, also serving as a ring clamp means. The tie 37a can be tensioned by a tool (not shown) known for this purpose, then the excess length of the tie is cut off.

Figure 4:
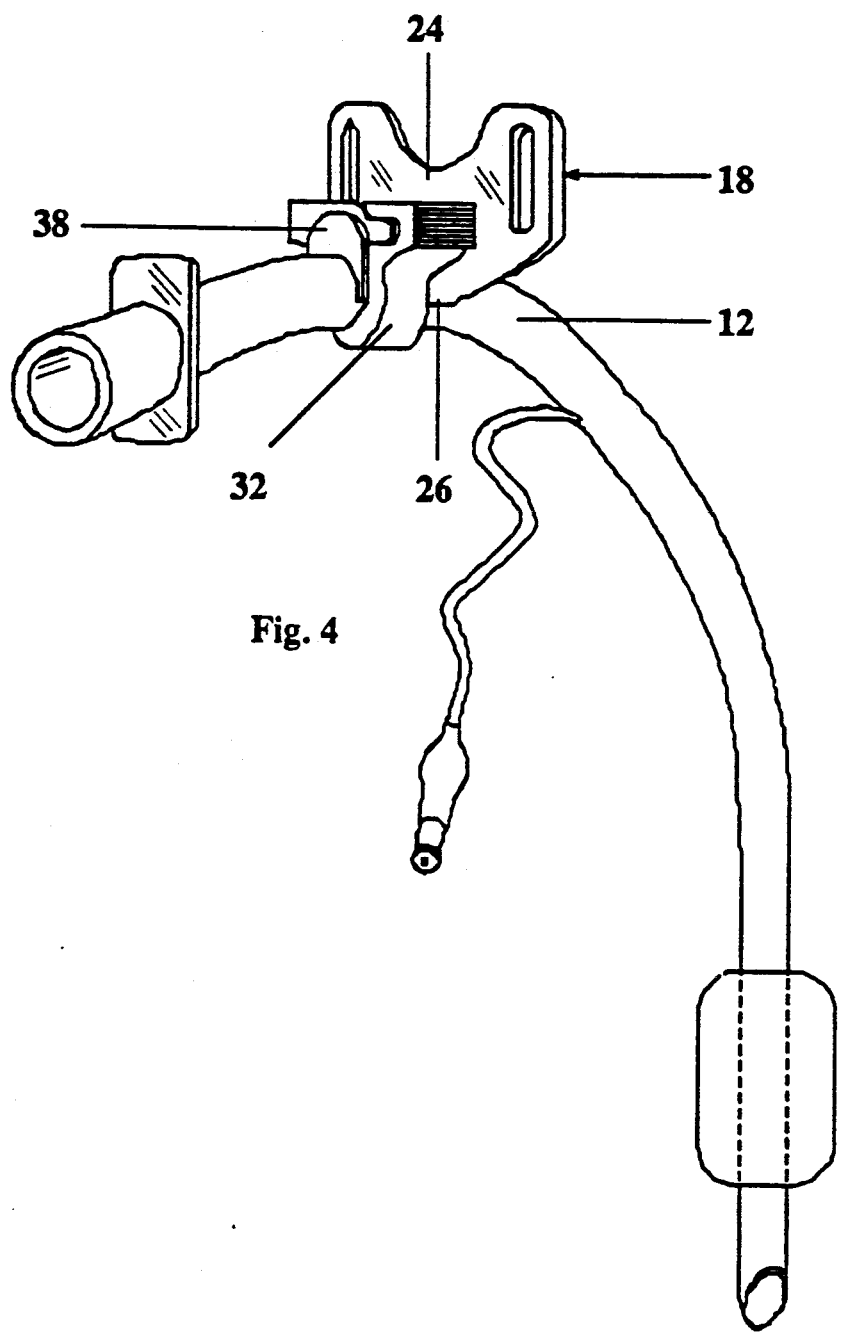
FIG. 4 is a perspective view showing an endotracheal tube with the lip-engaging member clamped to the tube.

FIG. 4 shows in perspective the engagement of the lip-engaging member 18 onto the tube 12 with the ring clamp 32. As illustrated in FIG. 4 and FIG. 3A, the collar 26 may have an outer flange 38 and an inner structural area 40 (FIG. 3A) at where the collar is secured to or extends from the platelike portion 24. As illustrated, the outer flange may have a height in excess of what is needed for retention of the ring clamp. This can be useful for engagement by the thumb in intubating the patient. It enables a convenient grip on the device as secured to the tube, by using the thumb and forefinger to hold the flange 38 and the back of the lip-engaging plate 24.

Figure 7:
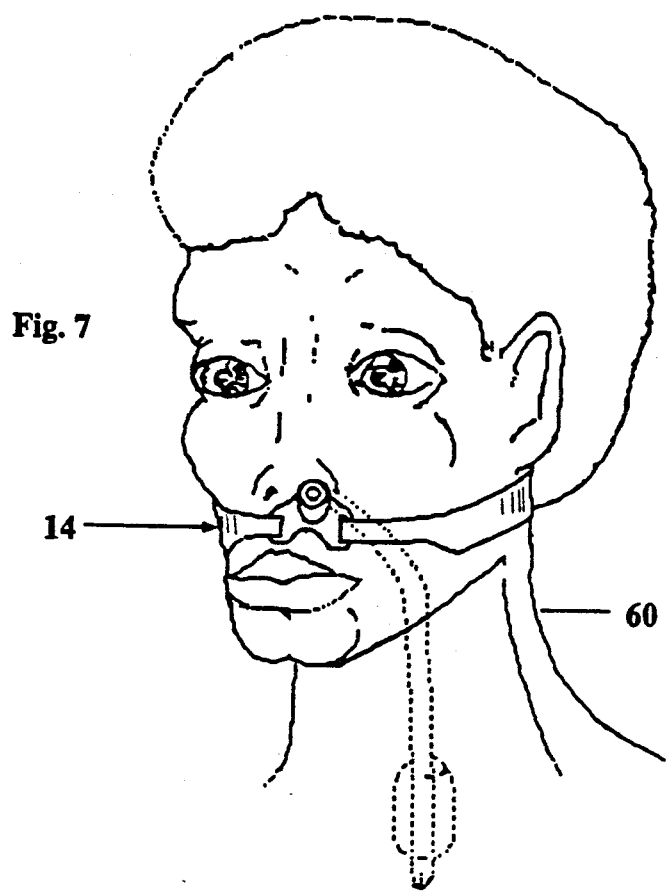
FIG. 7 is a view similar to FIG. 1 but showing the device of the invention used for nasal intubation.
Figure 6:
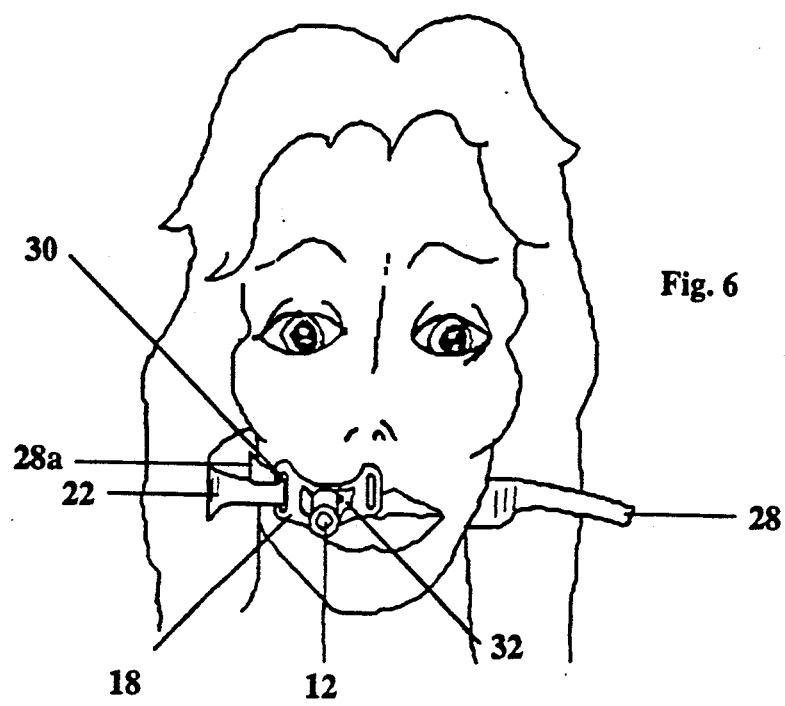
FIG. 6 is another view of a patient, showing a part of a preferred procedure for attaching the device to the patient.

As shown particularly in FIGS. 1, 2, 4 and 6, the slotted openings 30 of the wings of the lip-engaging member 18 are offset in height from the position the endotracheal tube takes in the collar. In oral intubation as shown in FIGS. 1 and 6, the slotted openings are on a line which lies significantly above the center line of the tube 12; in nasal intubation as shown in FIG. 7, a horizontal line through the slots would be below the tube. Thus, the ends of the tape band 22 engage the slots, and adhere to the patient's skin, at a position vertically offset from the location of the endotracheal tube 12 as intubated in the patient.

Figure 5:
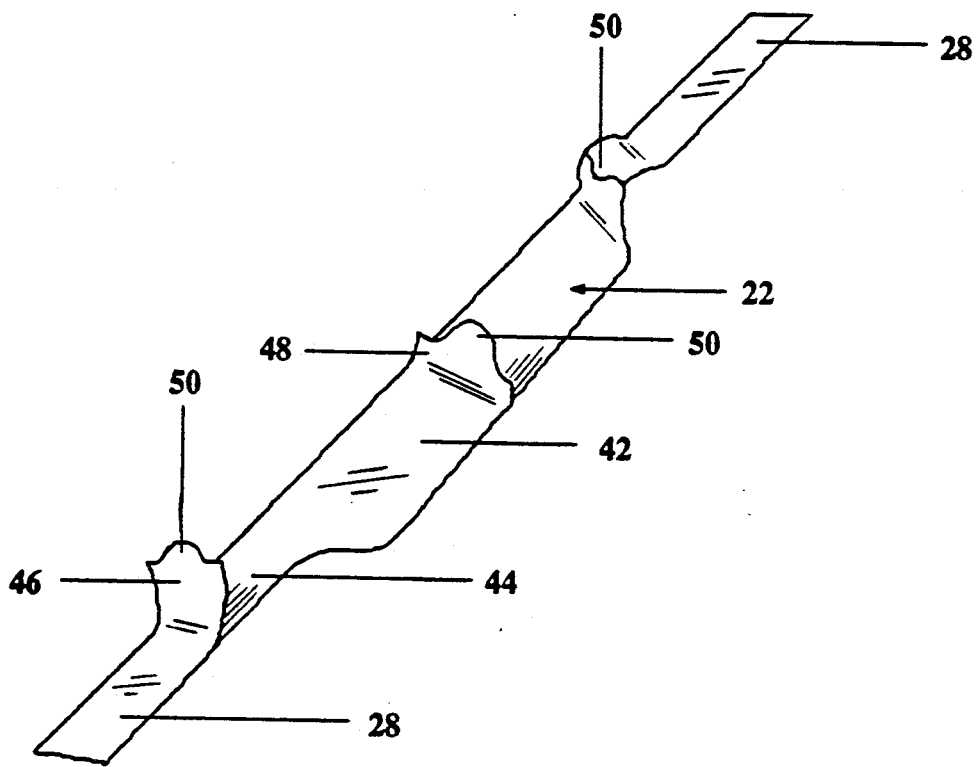
FIG. 5 is a plan view, partially in perspective, showing a tape band preferably used to retain the device properly on the patient, for correct location of the tube.

FIG. 5 shows a preferred configuration of the tape band 22 of the tube retention apparatus. It may be formed of plastic film similar to that of small stick-on bandages sold for home use. As illustrated, the tape band 22 may be tapered or reduced in width toward its ends 28, with a wider middle section 42 for engagement around the head. The length of the tape band 22, as mentioned above, preferably is in excess of what is needed for most patients, so that substantially all patients can be accommodated. The tape band has adhesive applied on one surface 44, which is the inner surface of the band when in position on a patient. This adhesive extends through at least most of the length of the tape band, and may be applied to the entire inner surface 44 if desired. However, the adhesive is covered by separate, discrete release strips or backing strips 46 and 48 at its central areas and end areas as illustrated. These may be separately released to expose adhesive as desired, for optimal positioning of the tube 12, maximum retention of the tube in proper position and maximum comfort to the patient.

As illustrated, the release strips 46 and 48 may each include a thumb tab 50 for gripping with the thumb or fingernail to individually remove these release strips. Although four release strips are shown in FIG. 5, a larger number can be provided if desired.

Figure 5A:
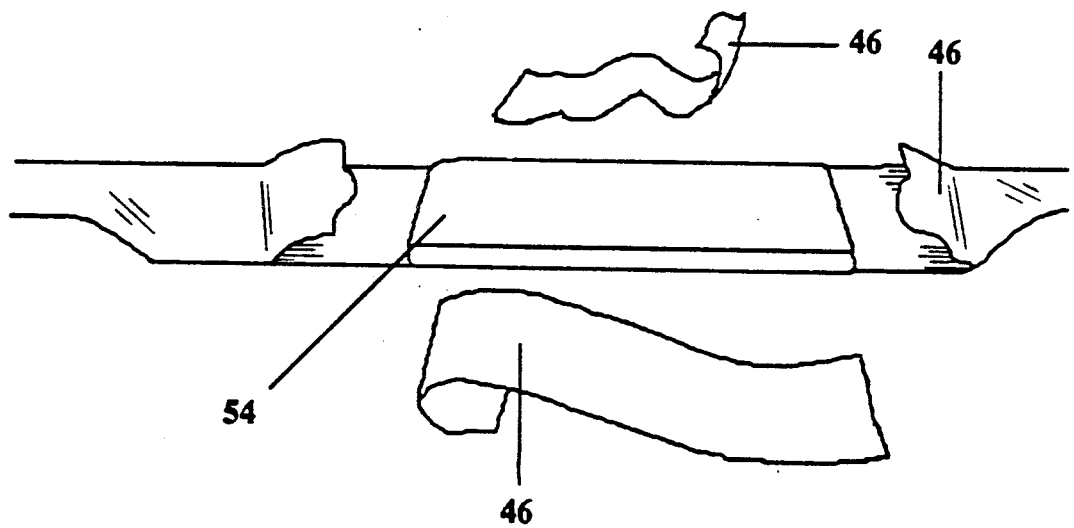
FIG. 5A is a plan view similar to FIG. 5 but showing an alternative embodiment.

In nearly all cases the central area of the tape band will contact hair at the back of the patient's head. For this reason, the band can be without adhesive in this central area or the adhesive can remain covered. In one preferred embodiment of the invention shown in FIG. 5A, absorbent gauze 54 is permanently retained on the band by the adhesive in this area. Release strips 46a can then be shorter as shown. The gauze is advantageous because it has a feel familiar to the patient, it adds comfort, it has some absorbency and it grips the hair better than a plastic surface.

FIG. 6 illustrates the preferred procedure for securing the endotracheal tube retaining system in place. The lip-engaging member 18 is first secured to the tube 12 in essentially the correct position and the clamp 32 is used to secure the member 18 and the tube 12 together. The tube is then held up near or against the palate in the desired position, and preferably to one side as illustrated in FIG. 6.

Then the tape band is brought around the head to a position generally representing the final position, with a substantial overlap of the ends in front. In a preferred procedure, the ends of the tape band are snipped off together by the therapist at the tube location, leaving the tape ends generally abutting at the tube. This gives sufficient end length to properly engage the remaining tape ends in the slots 30. Then the release strips are removed in those areas where the patient is to be contacted (ordinarily all areas excepting the hair line) and including at the end portions 28. Both ends 28 are secured to the lip-engaging member 18 using the slots as illustrated. The ends of the tape, with the exposed adhesive, are folded back against themselves to make a connection.

For patient comfort, or to prevent lesions or sores on the patient's skin, the tape band 22 may be removed, discarded and replaced with a new tape band as frequently as desired, without removing or changing the position of the lip-engaging member 18.

FIG. 7 shows the device 14 and system of the invention used for nasal intubation of a patient 60. As illustrated, the device fits comfortably on the patient, with minimal apparatus above the lip and at the nose.

The above described preferred embodiments are intended to illustrate the principles of the invention, but not to limit its scope. Other embodiments and variations to these preferred embodiments will be apparent to those skilled in the art and may be made without departing from the spirit and scope of the invention as defined in the following claims.

What is claimed is:

1. An apparatus for retaining an endotracheal tube properly in position on a patient, comprising,
   a soft flexible lip-engaging member having a soft plate-like portion, soft to the touch, for engaging against the patient and having a pair of left and right wings each having a slot for retention of the lip-engaging member, a tube engaging collar extending outwardly from the plate-like portion, and forming only part of a circle, the lip-engaging member being sized to engage essentially only the small area on the patient above the mouth opening and below the nasal openings, and the lip-engaging member extending substantially in only one direction from the endotracheal tube,
   ring clamp means for engagement about the collar and the tube with the tube engaging the collar for clamping the lip-engaging member in position on the tube, the ring clamp means directly contacting the tube on the side of the tube opposite the side contacting the collar to provide a lower profile where the ring clamp contacts the tube so as not to obstruct the mouth when used for oral intubation,
   a tape band of sufficient length to engage around the patient's head and to connect to the lip-engaging member and having a pair of end connection means for passing through the slots in the wings of the lip-engaging member for retention of the member, and the tape band having one surface coated with adhesive through most of its length,
   and the tape band having on said one surface a series of separately removable discrete release strips covering the adhesive, whereby the release strips may be separately removed to selectively engage the patient's skin at appropriate locations with the tape band extending around the back of the head and with the end connection means of the tape band inserted through and secured to the lip-engaging member.

2. The apparatus of claim 1, wherein the tape band tapers from a wider dimension in a central area to a narrower dimension at the two end connection means.

3. The apparatus of claim 1, wherein the slots in the soft lip-engaging member comprise generally vertical slots, and wherein the end connection means of the tape band comprise ends of lesser widths than the remainder of the tape band and having adhesive on said one surface, whereby the tape band ends may be inserted through the slots of the lip-engaging member and adhered back against the tape band to secure the member in place.

4. The apparatus of claim 1, wherein the flexible lip-engaging member is about one and one-half inches in width and no more than about one inch in height.

5. The apparatus of claim 1, wherein the flexible lip-engaging member is formed integrally of a soft rubbery silicone material.

6. The apparatus of claim 1, wherein the slots in the plate-like portion are offset from the position of the tube at the tube engaging collar such that the two slots lie generally on a line above the location of the tube in an oral intubation.

7. An apparatus for retaining an endotracheal tube properly in position on a patient, comprising,
   a soft flexible lip-engaging member having a soft plate-like portion, soft to the touch, for engaging against the patient, and having a pair of left and right wings each having a slot for retention of the lip-engaging member, a tube engaging collar extending outwardly from the plate-like portion, and forming only part of a circle, the two slots being offset from the position of the tube at the tube engaging collar such that the two slots lie generally on a line above the location of the tube in an oral intubation, and the lip-engaging member being sized to engage the small area on the patient above the mouth opening and below the nasal openings, and the lip-engaging member extending substantially in only one direction from the endotracheal tube,
   ring clamp means for engagement about the collar and the tube with the tube engaging the collar for clamping the lip-engaging member in position on the tube, the ring clamp means directly contacting the tube on the side of the tube opposite the side contacting the collar to provide a lower profile where the ring clamp contacts the tube so as not to obstruct the mouth when used for oral intubation, and
   tape means for engaging on the patient and for connecting to the lip-engaging member via the two slots, and having a pair of end connection means for passing through the slots in the wings of the lip-engaging member for retention of the member, and the tape means having one surface with adhesive coating for engaging against the patient's skin.

* * * * *